(12) United States Patent
Lange

(10) Patent No.: US 6,844,303 B2
(45) Date of Patent: Jan. 18, 2005

(54) CLEANING COMPOSITIONS AND THEIR USE IN FEMININE HYGIENE WIPES

(76) Inventor: Rainer Lange, Kirchstrasse 36, Bad Honnef (DE), 53604

( * ) Notice: Subject to any disclaimer, the term of this patent is extended or adjusted under 35 U.S.C. 154(b) by 168 days.

(21) Appl. No.: 10/017,251

(22) Filed: Dec. 14, 2001

(65) Prior Publication Data

US 2003/0114324 A1 Jun. 19, 2003

(51) Int. Cl.$^7$ .................................................. A61K 7/50
(52) U.S. Cl. ........................ 510/130; 510/137; 510/159; 510/438; 424/401; 15/201.1
(58) Field of Search ................................ 510/159, 137, 510/130, 156, 438; 424/401, 78.03; 15/201.1

(56) References Cited

U.S. PATENT DOCUMENTS

| | | | |
|---|---|---|---|
| 5,578,312 | A | 11/1996 | Parrinello |
| 6,139,828 | A | 10/2000 | McCullough |
| 6,174,533 | B1 | 1/2001 | SaNogueira, Jr. et al. |
| 6,294,182 | B1 | 9/2001 | Znaiden et al. |
| 6,306,408 | B1 | 10/2001 | Eichhorn et al. |
| 6,312,675 | B1 | 11/2001 | Deane |
| 6,338,855 | B1 | 1/2002 | Albacarys et al. |
| 6,409,657 | B1 | 6/2002 | Kawano |

2003/0069148 A1 * 4/2003 Booker et al. .............. 510/130

FOREIGN PATENT DOCUMENTS

| | | |
|---|---|---|
| DE | 44 04 790 C1 | 8/1995 |
| EP | 1 238 653 A1 | 9/2002 |

OTHER PUBLICATIONS

Frosch et al., "A Method for Appraising the Stinging Capacity of Topically Applied Substances", *Journal of the Society of Cosmetic Chemists*, vol. 28, ppgs. 197–209 (1977).
Simon, et al., "Sequential Order of Skin Responses to Surfactants During A Soap Chamber Test", *Contact Dermatitis*, vol. 25, ppgs. 242–249 (1991).
Frosch, et al., "The Soap Chamber Test," *Journal of American Acad. Of Dermatology*, vol. 1, ppgs. 35–41 (1979).
Kligman, et al., "A Method For the Measurement and Evaluation of Irritants on Human Skin," *Journal of Investigative Dermatology*, vol. 40, ppgs. 78–94 (1967).
European Search Report dated Oct. 4, 2003, for corresponding PCT/EP02/14280.

* cited by examiner

*Primary Examiner*—Necholus Ogden

(57) ABSTRACT

This invention relates to cleansing compositions and feminine hygiene wipes containing the cleansing composition. The cleansing composition comprises water; a humectant; a solubilizer; chamomile; and panthenol. The composition is not irritating and does not sting the skin.

13 Claims, No Drawings

CLEANING COMPOSITIONS AND THEIR USE IN FEMININE HYGIENE WIPES

BACKGROUND OF THE INVENTION

This invention relates to cleansing products and wipe products comprising a porous or absorbent sheet and a cleansing composition. The products are useful for many applications, in particular in feminine hygiene. The compositions are not stinging to the skin.

Wipe products have become an important product category that has found a wide variety of applications for adults and babies. Examples include face or body cleansing wipes, wipes for skin treatment, and skin conditioning wipes.

Over the last couple of decades, so-called wet wipes have become successful as products particularly suited for these applications. These products are typically manufactured by impregnating sheets made of non-woven fabric with a suitable lotion.

Recent innovations in the wipes area included improvements in the fabric, in the impregnating liquid, and in product presentation.

Initially, wet wipe products were made of traditional non-woven materials based on paper making technology (pulp based products). These products were well accepted but deficient in softness of the fabric material. The introduction of the 'spunlace' non-woven technology offered products that, compared to traditional paper based products, were superior in terms of softness. This is mainly due to (i) the use of long soft fibres (most frequently rayon and polyethylene terephthalate/polypropylene or a mixture of these fibres) in the spunlace process and (ii) the fact that during the spunlace process no binder is added to the fabric.

Another innovation was the introduction of the 'Pop-up' technology that offered advantages as regards to the dispensing of individual wipes.

Wipes are frequently loaded with compositions that cleanse and or moisturize the skin. During use, the wipes may contact sensitive areas, such as mucous membranes or the eyes. The compositions utilized frequently cause stinging or irritation to the sensitive areas. There is a need for a wipe that contains a cleansing composition that does not irritate or sting sensitive areas. Providing such products is an object of this invention.

This object is attained with the products provided herein, which cleanse the skin and sensitive areas, yet do not sting.

SUMMARY OF THE INVENTION

In one embodiment, the present invention provides a cleansing composition having water; a humectant; a solubilizer; chamomile; and panthenol.

In a second embodiment, the present invention concerns wipe products comprising a porous or absorbent sheet and a composition that contains water; a humectant; a solubilizer; chamomile; and panthenol. Preferably the composition is liquid and is coated onto or impregnated into the sheet.

DETAILED DESCRIPTION OF THE INVENTION

Whenever used in this description and claims, any percentage is weight by weight (w/w).

The sheet of absorbent or porous material for use in the products of this invention can take the form of a tissue, a wipe, towel, towelette, and the like. The material may be flushable. As used herein, by "flushable" is meant that the material will pass through at least 10 feet of waste pipe in two toilet flushes. The material may also be biodegradable.

Sheet materials that can be used can be mono or multi-layered, woven or non-woven. They can be made of one or of several materials. Particularly preferred are non-woven materials that have a web structure of fibrous or filamentous nature, in which the fibres or filaments are distributed randomly or with a certain degree of orientation, the former being obtainable by air-laying or by certain wet-laying processes, the latter by other wet-laying or by carding processes. The fibres or filaments can be natural, for example wood pulp, wool, cotton, linen and the like, or synthetic, for example polyvinyls, polyesters, polyolefins, polyamides and the like.

Typically they have a basis weight in the range of 10 to 80 $g/m^2$, in particular of 20 to 70 $g/m^2$. Particular materials are of the non-woven type. Based on the raw material that has been used, two different types of products can be distinguished.

A first type of carrier is paper based. The raw materials for these carriers are made almost exclusively of cellulose-based fibres or filaments from plant cellular sources (pulp). These can be available from fresh wood-shavings or from recycled material (recycled paper). In a number of wipe applications, such as baby wipes, wipes for cleansing, feminine hygiene wipes, wet paper towels and the like, high wet strength or firmness of the non-woven web is a desirable attribute. This can be achieved by the addition of binding materials. Examples of such materials are the so-called wet strength resins. In some cases additives are added in order to increase the softness of the end product.

In a second type use the web is made mainly of staple fibers, e.g. based on cotton, wool, linen and the like.

Commercial products are made of cellulose fibres, synthetic fibres or mixtures of both. Polyester and polypropylene are known as suitable polymers for the preparation of synthetic fibres. Also in these products, binders can be used to increase the firmness of the non-woven fabric.

Webs of increased strength can be obtained by using the so-called spunlace or hydro-entanglement technique. In this technique the individual fibres are twisted together so that an acceptable strength or firmness is obtained without using binding materials. The advantage of the latter technique is the excellent softness of the non-woven material.

Non woven materials that are made of a mixture of pulp and staple are also known. Such materials are available with binding materials, in particular those mentioned above, or without binding materials. In the latter instance the non-woven is preferably made by the spunlace or hydro-entanglement procedure.

In one embodiment of the present invention, the carrier material is made of cellulose pulp with a small amount of binding material. The amount of binder in the carrier material may range from about 5 to about 20% (w/w).

In another embodiment, the non-woven fabric is prepared by the hydro-entanglement procedure and does not contain binding material.

The absorbing ability of the carrier material is of particular interest with regard to the applications envisaged by the present invention. During production the impregnating solution should be taken up quickly by the carrier. In certain embodiments of this invention the wipes will be packed in a stack of a plurality of wipes. In this instance the absorbing ability of the non-woven fabric should be such that a chromatographic effect (sinking down of the lotion) in the stack is avoided during storage. On the other hand it should be guaranteed that during the usage of the wipe the liquid composition is delivered evenly to the skin.

The absorbing capacity of the carrier material is determined essentially by three different parameters: the basis weight of the carrier material, the nature of the raw material used in the manufacture and the manufacturing process used.

For the applications according to the invention the carrier materials typically have a basis weight from 10 g/m² to 80 g/m², preferably from 30 to 70 g/m² and more preferably from 40 to 60 g/m². The selection of the raw material of which the non-woven carrier is made depends on the manufacturing procedure. Typically in the manufacture of non-woven carriers by the hydro-entanglement process, use is made of mixtures of cellulose fibres and synthetic fibres. The relative quantity of synthetic fibres in the non-woven fabric is from 0 to 100% and preferably is between 10 and 70%, more preferably in the range of 30 to 50% (all percentages being w/w).

The products of the present invention further comprise a composition containing water; a humectant; a solubilizer; chamomile; and panthenol In particular, the compositions in the products of the invention are liquid compositions. They can be water-based formulations, in particular they can take the form of aqueous solutions. Preferably, the solutions are clear.

Alternatively, the liquids may be emulsion-based. These liquid compositions, which also are referred to as 'lotions', preferably are of aqueous nature.

The emulsions can be oil-in-water or water-in-oil emulsions, or be of more complex nature such as water-in-oil-in-water. The emulsions may be made by methods known in the art, including the known phase inversion technique.

The compositions for use in the products of the invention contain water. The amount of water may range from about 50 to about 97%, preferably from about 70 to about 97%, more preferably from about 85 to about 97% by weight of the total composition.

The composition of the invention contains chamomile and panthenol as active ingredients that help reduce irritation or stinging and smooth skin, as well as provide other known benefits. The amount of panthenol may range from about 0.2 to about 5%, preferably from about 0.3 to about 2%, more preferably from about 0.3 to about 1% by weight of the total composition. The amount of chamomile may range from about 0.05 to about 5%, preferably from about 0.1 to about 2%, more preferably from about 0.1 to about 1% by weight of the total composition. The ability of a composition to sting the skin (and, conversely, the ability of a composition to be non-stinging) can be determined, e.g., according to the method described in Peter J. Frosch and Albert M. Kligman, "The Soap Chamber Test", *Journal of American Acad. of Dermatology*, Volume 1, pp. 35–41 (1979); Peter J. Frosch and Albert M. Kligman, "A method for Appraising the Stinging Capacity of Topically Applied Substances", *Journal of the Society of Cosmetic Chemists*, Volume 28, pp. 197–209 (1977); F. Anthony Simon et al., "Sequential Order of Skin Responses to Surfactants During a Soap Chamber Test", *Contact Dermatitis*, Volume 25, pp. 242–249 (1991); and A. M. Kligman and W. M. Wooding, "A Method for the Measurement and Evaluation of Irritants on Human Skin", *The Journal Investigative Dermatology*, Volume 40, pp. 78–94 (1967).

At least one solubilizer is utilized to solubilize the panthenol and the chamomile, as well as to provide cleansing action. Anionic, cationic, amphoteric, betaine, and nonionic solubilizers may be utilized, as well as combinations thereof. Preferably, due to irritation and stinging concerns, the composition is free of anionic, cationic, amphoteric, and betaine solubilizers. As used herein, free of anionic, cationic, amphoteric, and betaine solubilizers means that the composition contains less than about 2%, preferably less than 1%, more preferably less than 0.5%, and most preferably less than about 0.1% by weight of each anionic, cationic, amphoteric, and betaine solubilizer, based on the total weight of the composition.

As used herein, betaines are derived from alkyl amidopropyl dimethylamine. They can exist in only two forms: cationic at low pH and isoelectric at intermediate pH. Suitable betaine solubilizers for the compositions of the invention include, but are not limited to, alkyl betaines, amidoalkyl betaines, phosphobetaines, pyrophosphobetaines, and mixtures thereof. Cocamidopropylbetaine is a preferred betaine.

Amphoteric solubilzers may also be used in the compositions of the present invention. As used herein, amphoteric solubilizers are derivatives of alkyl hydroxyethyl imidazolines formed through a reaction with sodium chloroacetate. They are true amphoterics in that they exist in three different forms depending on pH: cationic at low pH, zwitterionic at intermediate pH, and anionic at high pH. Suitable amphoterics include, but are not limited to, amphocarboxylates, amidoalkyl sultaines, amphophosphates, carboxyalkyl alkyl polyamines, and mixtures thereof. Lauroamphodiacetate is a preferred amphoteric.

Anionic solubilizers may also be utilized in the compositions of the present invention. Suitable anionic solubilizers include sulfate and carboxylate containing solubilizers, such as sodium lauryl sulfate and the like.

Nonionic solubilizers are preferred. One class of nonionic solubilizers useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Delaware under the tradename "Tween® 20."

The amount of nonionic solubilizer present in the compositions of the present invention may range from about 0.5 to about 5%, preferably from about 1 to about 3%, more preferably from about 1 to about 2% by weight, based on the total weight of the composition.

The compositions of the present invention include a humectant. Suitable humectants include propylene glycol, dipropylene glycol, glycerine, and the like. The amount of humectant may range from about 0.4 to about 5%, preferably from about 0.6 to about 3%, more preferably from about 0.6 to about 1% by weight, based on the total weight of the composition. All percentages in this and the preceding paragraph are w/w percentages.

The amount of the composition on the wipe will be in the range from about 100 to about 400%, preferably from about 200% to about 400%, expressed as the weight of the composition relative to the weight of the sheet in dry condition.

The compositions for use in the products of the invention may further contain skin care and/or active ingredients like emollients, oils, plant extracts, vitamins, etc. Oils can be of natural or synthetic origin, e.g. vegetable oils or mineral oils or the group of silicones.

The group of emollients comprises lipids like lanolin, lanolin alcohols, lanolin acids, polyethoxylated or acylated lanolin or lanolin derivatives, lecithin and lecithin derivatives, fatty alcohols, either linear or branched with chain lengths between C6 and C40, and their esters with organic acids, e.g. carbonic acids or polyacids containing between 2 and 30 C atoms, branched, aromatic or linear including hydroxy or amino acids, fatty acids and fatty acid esters with alcohols or poly alcohols containing between 2 and 40 C atoms, branched, aromatic or linear, sterols found in the unsaponifiable fraction of e.g. avocado oil, almond oil, soybean oil, etc. like soy phytosterol, β-sitosterol, β-sitosteryl laurate, β-sitosteryl stearate, etc. natural and synthetic waxes, e.g. bees wax, purcelline, shea butter, cocoa butter, ceresin, ozokerit, vaseline, micro wax, carnauba wax, candelilla wax and the like, substituted cyclohexanes like di-n-octylcyclohexane, Guerbet carbonates, e.g. bis-2-octyl dodecylcarbonate, dialkyl ethers like di-n-octyl ether, etc.

Examples of oils are natural oils, e.g. almond oil, soybean oil, wheat germ oil, avocado oil, jojoba oil, linseed oil, sesame oil, walnut oil, sunflower oil, olive oil, etc., mineral and paraffin oil and synthetic oils comprising mono-, di-, triglycerides as well as mixtures thereof.

The compositions may also contain film-forming substances like chitosan and derivatives thereof, derivatives of poly acrylic acid, polyvinyl pyrrolidone and its derivatives, etc.

As mentioned above, the compositions may further contain active ingredients such as anti-microbials (antibacterials and antifungals), anti inflammatory agents, anti irritating compounds, sunscreen agents, moisturising agents, anti-wrinkle agents, plant extracts, vitamines, and the like. Examples of such ingredients comprise complexes of PVP and hydrogen peroxide, diclofenac, acetyl salicylic acid, salicylates, ibuprofen, bisabolol, mimosa extract (mimosa tenuiflora), hyaluronic acid, chondroitin sulfate, bisabolol, tocopherol, actives for anti-stinging, anti-irritants, anti-dandruffs, anti-ageing agents e.g. retinol, melibiose etc. Other suitable actives are e.g. medicago officinalis, actinidia chinensis, allantoin, aloe barbadensis, anona cherimolia, anthemis nobilis, arachis hypogaea, arnica montana, avena sativa, beta-carotene, bisabolol, borago officinalis, butylene glycol, calendula officinalis, camellia sinensis, camphor, candida bombicola, capryloyl glycine, carica papaya, centaurea cyanus, cetylpyridinium chloride, chenopodium quinoa, chinchona succirubra, chondrus crispus, citrus aurantium dulcis, citrus grandis, citrus limonum, cocos nucitera, coffea arabica, crataegus monogina, cucumis melo, dichlorophenyl imidazoldioxolan, enteromorpha compressa, equisetum arvense, ethoxydiglycol, ethyl panthenol, farnesol, ferulic acid, fragaria chiloensis, gentiana lutea, ginkgo biloba, glyceryl laurate, glycyrrhiza glabra, hamamelis virginlana, heliotropine, hydrogenated palm glycerides, citrate, hydrolyzed castor oil, hydrolyzed wheat protein, hypericum perforatum, iris florentina, juniperus communis, lactis proteinum, lactose, lawsonia inermis, linalool, linum usitatissimum, lysine, magnesium aspartate, magnifera indica, malva sylvestris, mannitol, mel, melaleuca alternifolia, mentha piperita, menthol, menthyl lactate, mimosa tenuiflora, nymphaea alba, olaflur, oryza sativa, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, persea gratissima, petrolatum, potassium aspartate, potassium sorbate, prunus amygdalus dulcis, prunus armeniaca, prunus persica, retinyl palmitate, ricinus communis, rosa canina, rosmarinus officinalis, rubus idaeus, salicylic acid, sambucus nigra, sarcosine, serenoa serrulata, simmondsia chinensis, sodium carboxymethyl betaglucan, sodium cocoyl amino acids, sodium hyaluronate, sodium palmitoyl proline, stearoxytrimethylsilane, stearyl alcohol, sulfurized TEA-ricinoleate, talc, thymus vulgaris, tilia cordata, tocopherol, tocopheryl acetate, trideceth-9, triticum vulgare, tyrosine, undecylenoyl glycine, urea, vaccinium myrtillus, valine, zinc oxide, zinc sulfate.

In one embodiment of the present invention, the products are useful as feminine hygiene wipes. These wipes are useful for cleansing intimate or sensitive areas. In order to reduce irritation associated with cleansers utilized in such areas, the pH of the composition should be maintained from about 4 to about 6, preferably from about 4.5 to about 6, most preferably, about 5 to about 6. The pH may be adjusted with any acid, for example citric acid, lactic acid, and the like. Lactic acid is preferred.

The wipe products according to the invention can be made by coating the said composition onto or impregnating it into the sheet material. The term coating also comprises techniques such as printing and spraying of the composition on the sheet.

The compositions for use in the products of the invention are prepared by conventional methods. Alternatively, a concentrate may be made which subsequently is diluted with a suitable aqueous medium to obtain the composition, which is applied to the sheet.

In a particular execution, the carrier material is cut into strips the transversal size of which being similar to the size of the sheet, in particular the tissue or wipe. Subsequently the carrier strips are folded according to methods generally known and applied in the art. The thus folded strips are moistened with a liquid composition as defined herein, said moistening preferably comprising spraying or dripping. Or the fabric strips can first be moistened and subsequently be folded.

The strips can also be impregnated with the composition by immersing in or running the strip through a bath containing the composition. They can also be sprayed or printed with the composition.

In a further step, the strips are cut so that the desired size of the sheets, in particular of the wipes, is obtained. The thus obtained sheets (or wipes) can be packed individually or can be stacked in a determined number, e.g., a number between 10 and 30, preferably between 15 and 25, most preferably about 20, or a number between 50 and 100, preferably between 60 and 80, most preferably about 72, and the stack then packed in a suitable package, for example a plastic wrap, box and the like.

The products according to the invention can take the form of baby or adult wipes and can be used in a wide range of applications as personal care products, comprising, for example, baby cleansing wipes, face or body cleansing wipes, feminine hygiene wipes, wipes for skin treatment or skin conditioning such as for example skin moisturization, insect repellent wipes, sunscreen wipes, and the like.

The products of the invention are non-stinging to sensitive areas.

As used herein applying or application to the skin comprises any action contacting the product to the skin e.g. by rubbing across the skin, bathing, dabbing, wetting and the like.

EXAMPLE 1

The following materials were combined in a vessel and stirred until dissolved:

| | |
|---|---|
| Propylene Glycol | 0.8% |
| Tween ® 20 (polysorbate 20) | 1.5% |
| Phenoxyethanol | 1.0% |
| Nipaguard IPF ™ (iodopropynyl butyl Carbamate) | 0.1% |
| Fragrance | 0.2% |
| Water | 94.28% |
| Extrapone Chamomile Special P (10% chamomile) | 1.5% |
| D-Panthenol | 0.6% |
| Silicone antifoam 1510 | 0.015% |
| Lactic acid (80%) | 0.00525% |

The resulting cleansing composition was a clear liquid with a pH of 5.44.

EXAMPLE 2

The following materials were combined in a vessel and stirred until dissolved:

| | |
|---|---|
| Propylene Glycol | 0.8% |
| Tween ® 20 (polysorbate 20) | 0.8% |
| Phenoxyethanol | 0.7% |
| Nipabutyl (butyl paraben) | 0.075% |
| Methyl paraben | 0.16% |
| Propyl paraben | 0.10% |
| Fragrance | 0.2% |
| Water | 95.07% |
| Extrapone Chamomile Special P (10% chamomile) | 1.5% |
| D-Panthenol | 0.6% |
| Lactic acid (80%) | 0.005% |

The resulting cleansing composition was a cloudy liquid with a pH of 4.8

EXAMPLE 3

The following materials were combined in a vessel and stirred until dissolved:

| | |
|---|---|
| Propylene Glycol | 0.8% |
| Tween ® 20 (polysorbate 20) | 0.8% |
| Phenoxyethanol | 1.0% |
| Nipaguard IPF ™ (iodopropynyl butyl Carbamate) | 0.1% |
| Fragrance | 0.2% |
| Water | 95.00% |
| Extrapone Chamomile Special P (10% chamomile) | 1.5% |
| D-Panthenol | 0.6% |
| Lactic acid (80%) | 0% |

The resulting cleansing composition was a cloudy liquid with a pH of 5.24.

EXAMPLE 4

The following materials were combined in a vessel and stirred until dissolved:

| | |
|---|---|
| Propylene Glycol | 0.8% |
| Tween ® 20 (polysorbate 20) | 0.8% |
| Phenoxyethanol | 1.0% |
| Nipaguard IPF ™ (iodopropynyl butyl Carbamate) | 0.1% |
| Fragrance | 0.2% |
| Water | 95.595% |
| Extrapone Chamomile Special P (10% chamomile) | 1.5% |
| D-Panthenol | 0% |
| Lactic acid (80%) | 0.005% |

The resulting cleansing composition was a cloudy liquid with a pH of 4.97.

EXAMPLE 5

The following materials were combined in a vessel and stirred until dissolved:

| | |
|---|---|
| Propylene Glycol | 0.8% |
| Tween ® 20 (polysorbate 20) | 1.0% |
| Phenoxyethanol | 1.0% |
| Nipaguard IPF ™ (iodopropynyl butyl Carbamate) | 0.1% |
| Fragrance | 0.2% |
| Water | 94.8% |
| Extrapone Chamomile Special P (10% chamomile) | 1.5% |
| D-Panthenol | 0.6% |
| Lactic acid (80%) | 0% |

The resulting cleansing composition was a clear liquid with a pH of 5.33.

EXAMPLE 6

The following materials were combined in a vessel and stirred until dissolved:

| | |
|---|---|
| Propylene Glycol | 0.8% |
| Tween ® 20 (polysorbate 20) | 1.5% |
| Phenoxyethanol | 1.0% |
| Nipaguard IPF ™ (iodopropynyl butyl Carbamate) | 0.1% |
| Fragrance | 0.2% |
| Water | 94.3% |
| Extrapone Chamomile Special P | 1.5% |

-continued

| | |
|---|---|
| (10% chamomile) | |
| D-panthenol | 0.6% |
| Lactic acid (80%) | 0% |

The resulting cleansing composition was a clear liquid with a pH of 5.29.

EXAMPLE 7

The following materials were combined in a vessel and stirred until dissolved:

| | |
|---|---|
| Propylene Glycol | 0.8% |
| Tween ® 20 (polysorbate 20) | 1.5% |
| Phenoxyethanol | 1.0% |
| Nipaguard IPF ™ (iodopropynyl butyl Carbamate) | 0.1% |
| Fragrance | 0.2% |
| Water | 94.29% |
| Extrapone Chamomile Special P (10% chamomile) | 1.5% |
| D-Panthenol | 0.6% |
| Lactic acid (80%) | 0.0095% |

The resulting cleansing composition was a clear liquid with a pH of 5.41.

EXAMPLE 8

Spunlace carrier material made of 65% rayon/35% polyester fabric having a surface weight of 55 g/m² was cut into strips. The strips were sprayed in the conventional manner with the liquid as prepared in example 1. Liquid addition was set at 5 g per wipe. Subsequently the strips were folded and cut.

EXAMPLE 9

A composition of the invention was tested for stinging as follows: The composition of Example 1 was applied to the face of each test subject, and stinging was rated at 2.5 minutes and 5 minutes. A scale of 0 being no stinging and 3 being severe stinging was utilized. A control sample of 10% lactic acid was compared to the composition of the invention. The samples were tested on twelve people. The composition of the invention demonstrated no potential for skin stinging. The lactic acid solution was found to be severely stinging.

I claim:

1. A cleansing composition comprising:
   about 0.4 to about 5% of a humectant wherein the humectant is selected from the group consisting of propylene glycol, dipropylene glycol, and glycerine; about 0.5 to about 5% of a solubilizer wherein the solubilizer is a nonionic solubilizer; about 0.05 to about 5% chamomile;
   about 0.2 to about 5% panthenol; and
   water, the percentages expressed as weight-percent based on the total weight of the composition, and the composition is free of anionic, cationic, amphoteric, and betaine solubilizers.

2. The composition according to claim 1 wherein the solubilizer is polysorbate 20.

3. The composition according to claim 2 wherein the pH of the composition ranges from about 4 to about 6.

4. The composition according to claim 3 wherein the pH of the composition ranges from about 4.5 to about 6.

5. The composition according to claim 4 wherein lactic acid is utilized to adjust the pH of the composition.

6. A feminine hygiene wipe comprising a substrate and a cleansing composition comprising:
   about 0.4 to about 5% of a humectant wherein the humectant is selected from the group consisting of propylene glycol, dipropylene glycol, and glycerine;
   about 0.5 to about 5% of a solubilizer wherein the solubilizer is a nonionic solubilizer;
   about 0.05 to about 5% chamomile;
   about 0.2 to about 5% panthenol; and water, the percentages expressed as weight-percent based on the total weight of the composition and, and the composition is free of anionic, cationic, amphoteric, and betaine solubilizers.

7. The wipe according to claim 6 wherein the solubilizer is polysorbate 20.

8. The wipe according to claim 7 wherein the pH of the composition ranges from about 4 to about 6.

9. The wipe according to claim 8 wherein the pH of the composition ranges from about 4.5 to about 6.

10. The wipe according to claim 9 wherein lactic acid is utilized to adjust the pH of the composition.

11. The wipe according to claim 6 wherein the basis weight of the substrate ranges from about 40 to about 60 g/m².

12. The wipe according to claim 11 wherein the amount of the composition on the wipe ranges from about 100 to about 400%, expressed as the weight of the composition relative to the weight of the substrate in dry condition.

13. The wipe according to claim 12 wherein the amount of the composition on the wipe ranges from about 200 to about 400%, expressed as the weight of the composition relative to the weight of the substrate in dry condition.

* * * * *